United States Patent [19]
Wilson

[11] Patent Number: 6,050,980
[45] Date of Patent: Apr. 18, 2000

[54] THROMBORESISTANT PLASTIC ARTICLE AND METHOD OF MANUFACTURE

[75] Inventor: Joseph E. Wilson, Dallas, Tex.

[73] Assignee: My-Tech, Inc

[21] Appl. No.: 09/128,358

[22] Filed: Aug. 3, 1998

[51] Int. Cl.[7] .................................................. A61M 5/32
[52] U.S. Cl. ......................... 604/265; 604/264; 427/2.1; 427/2.25; 427/2.3; 427/386
[58] Field of Search ..................... 424/423, 424, 424/425, 426, 422, 443, 445; 523/112, 113; 604/90.1, 113, 91.1, 265, 264, 403; 623/1, 2, 3, 11, 12; 427/2.1, 2.11, 2.12, 2.13, 2.24, 2.25, 2.3, 386

[56] References Cited

U.S. PATENT DOCUMENTS

| | | |
|---|---|---|
| 4,331,697 | 5/1982 | Kudo et al. ................................. 427/2 |
| 4,560,579 | 12/1985 | Siadat et al. ............................ 427/45.1 |
| 4,743,470 | 5/1988 | Nachtkamp et al. .................... 427/246 |
| 5,004,461 | 4/1991 | Wilson .................................... 604/265 |
| 5,126,140 | 6/1992 | Ito et al. .................................. 424/423 |
| 5,238,968 | 8/1993 | Morita et al. .............................. 521/79 |
| 5,834,007 | 11/1998 | Kubuta .................................... 424/443 |

*Primary Examiner*—Wynn Wood Coggins
*Assistant Examiner*—LoAn H. Thanh
*Attorney, Agent, or Firm*—Charles D. Gunter

[57] ABSTRACT

Antithrombotic agents having reactional functional groups are reacted with a base polymer also having reactive functional groups to form a surface coating for a medical material. The medical materials are used in medical devices in contact with blood or blood products such as artificial hearts, heart lung machines, pacemakers, vascular graft tubing, intra-aortic balloons, blood bags, soft or hard tissue prostheses, catheters, sutures, artificial organs, and the like.

17 Claims, 1 Drawing Sheet

THROMBORESISTANT PLASTIC ARTICLE AND METHOD OF MANUFACTURE

BACKGROUND OF THE INVENTION

1. Field of the Invention

The present invention relates generally to plastic medical instruments and devices having improved blood compatibility and, specifically, to devices having improved thromboresistant properties for the prevention of formation of harmful thrombi in the presence of blood or blood products.

2. Description of the Prior Art

Medical plastic materials which directly contact blood or blood products are required to possess blood compatibility and biocompatibility, as well as certain mechanical properties including flexibility, elasticity and durability. At present there are many types of medical instruments or devices requiring antithrombotic and thus hemocompatible surface properties. Examples include the arterial graft, artificial heart, heart-lung machine, pacemaker, artificial heart valve, vascular graft tubing, and intra-aortic balloon. When blood comes in contact with such materials foreign to the human body a number of processes result, including fibrin production and platelet activation. Each activated platelet tends to adhere to adjacent platelets thus forming aggregates. Each clump of platelets, with interwoven strands of fibrin, makes up a "thrombus." Thrombus formation is quite dangerous because it can obstruct the flow of blood to vital organs causing stroke or death.

One prior art technique for addressing the problem of fibrin production and platelet activation has been the periodic administration of antithrombotic agents to the patient orally or by intravenous injection. This technique is inconvenient because the treatment has only a short-term beneficial effect and must soon be repeated. Also, while the formation of thrombi may be reduced, the pharmacological action spreads over the whole body and adverse side effects may result.

Because of the drawbacks of oral or intravenous administration of antithrombotic agents, various coating techniques have also been attempted. A heparin coating on a medical device can give it short-term hemocompatibility, but heparin tends to wash away in the blood because of its water solubility. Covalently bound heparin has more permanence but any type of internal heparinized surface may lead to thrombocytopenia (J. E. Nelson, Arch. Intern. Med., 138, 548 (1978)).

Another approach to hemocompatibility is the use of a polyethylene oxide surface coating which prevents platelet attachment. However, this type of coating repels cell overgrowth, making it unsatisfactory for use on vascular grafts or coronary stents, which are intended to attract cell overgrowth.

One technique used for conferring long-term hemocompatibility involves encouraging the growth of a layer of endothelial cells over the surface of the implanted device. Such growth occurs after first immobilizing extracellular matrix (ECM) proteins on the surface of the device. However, cell overgrowth is a rather slow process even on a prepared surface. In one study, for example, an expanded polytetrafluoroethylene graft required 180 days to attain 96 percent of cell overgrowth coverage.

It has also been found that some degree of hemocompatibility results from a surface coating of immobilized phosphorylcholine. Another approach to hemocompatibility is the use of albumin-binding coatings, since albumin is known to inhibit fibrinogen adsorption in vitro and in vivo. Coatings containing plasminogen activators such as polysine, streptokinase, and urokinase are also known to inhibit clotting, since activated plasminogen dissolves fibrin as it forms.

Despite these advances in the art, a need exists for a simplified technique for rendering plastic medical devices of the above type thromboresistant, which technique is reliable, cost effective and which can be easily performed with commonly available starting materials.

Accordingly, it is an object of the present invention to provide a simple process for the manufacture of plastic medical instruments and devices having properties which resist thrombus formation and the activation of platelets which would otherwise degrade the functions of medical instruments and devices or lead to the manifestation of complications in the living body.

SUMMARY OF THE INVENTION

A thromboresistant plastic article is shown which includes a body formed with at least one exposed surface for contacting blood or blood products. The exposed surface of the body has a surface coating applied thereto. The surface coating comprises the reaction product of a base polymer containing epoxy groups and an antithrombotic agent containing hydroxyl groups. Preferably, the antithrombotic agent is selected from the group consisting of benzothiazolol, salicylaldoxime, ricinoleic acid, glyoxalbis (2-hydroxyanil), N-(2-hydroxyethyl) pyrrolidine, pinacol, and combinations thereof.

The surface coating also preferably includes a catalyst which promotes a reaction between the epoxy groups of the base polymer and the hydroxyl groups of the antithrombotic agent and a solvent for forming a homogeneous solution of the base polymer, antithrombotic agent and catalyst. Preferred catalysts include tetramethyl pyrazine, benzimidazole, and indazole. A plasticizer can also be present.

The base polymer can be prepared, for example, from glycidyl methacrylate as a suitable monomer having an epoxy group as a reactive functional group. A particularly preferred base polymer is a terpolymer having the following approximate percentage composition of monomers by weight, based on the total weight of terpolymer: 82% vinyl chloride, 9% vinyl acetate and 9% glycidyl methacrylate.

In the method of the invention, a polymeric body having at least one exposed surface is rendered thromboresistant. A solution is first prepared which includes as ingredients at least a base polymer having reactive epoxy functional groups and an antithrombotic agent having reactive hydroxyl functional groups. The base polymer and the antithrombotic agent are allowed to react in solution to thereby form as a reaction product a surface coating which will adhere to the exposed surface of the polymeric body. The surface coating is then applied to at least a portion of the exposed surface of the polymeric body. Again, the preferred antithrombotic agent is selected from the group consisting of benzothiazolol, salicylaldoxime, ricinoleic acid, glyoxalbis (2-hydroxyanil), N-(2-hydroxyethyl) pyrrolidine, pinacol, and combinations thereof.

The body which is rendered thromboresistant can be selected from the group consisting of catheters, sutures, blood bags, intra-aortic balloons, soft tissue prothesis, hard tissue prothesis, artificial heart and artificial organs.

Additional objects, features and advantages will be apparent in the written description which follows.

DETAILED DESCRIPTION OF THE INVENTION

Figure 1:
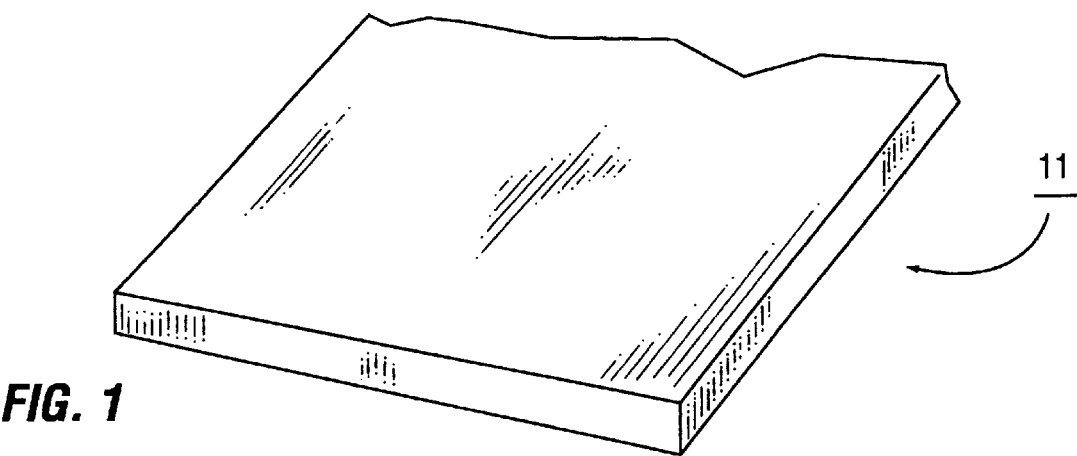
FIG. 1 is a perspective view, partly broken away, of a sheet of plastic film of the type which might be rendered thromboresistant by the method of the present invention.

The technique of the invention can be applied to a variety of medical materials to render such materials thromboresistant. The preferred materials are organic polymeric materials. Example organic polymeric materials include polyolefins, modified polyolefins, polyethers, polyurethanes, polyamides, polyesters and copolymers thereof. FIG. 1 shows a sheet of polyurethane film, designated as 11, which can be rendered thromboresistant according to the teachings of the present invention.

In contrast to certain of the previously described techniques, the present invention is designed to render surfaces of the above type thromboresistant by the simple application of a polymeric coating having the following ingredients: (1) a base polymer containing a first type of reactive functional groups which are preferably epoxy groups; (2) an antithrombotic agent containing a second type of reactive functional groups which are preferably hydroxyl groups; (3) a catalyst to promote reaction between the epoxy groups of the base polymer and the hydroxyl groups of the antithrombotic agent, and (4) a solvent combination to dissolve all components and form a homogeneous solution.

Before usage the thus formulated solution is allowed to stand for a time sufficient for the reactive functional groups to react and form a reaction product. This time can range from a matter of hours to several days at room temperature to allow time for the hydroxyl groups of the antithrombotic agent to react with the epoxy groups of the polymer.

The preferred functional groups for the base polymer are epoxy groups. It is convenient to start the formulation of all coatings used in the practice of the invention with the preparation of a "Standard Solution" based on a terpolymer having the following percentage composition of monomers by weight: 82% vinyl chloride, 9% vinyl acetate, and 9% glycidyl methacrylate. The Standard Solution should contain the following ingredients in the weight percentages shown:

| | |
|---|---|
| Terpolymer | 40% |
| Methyl ethyl ketone | 36% |
| Toluene | 24% |
| Total | 100% |

The Standard Solution can be prepared in any convenient manner, for example, by polymerizing the monomeric ingredients in the correct proportions to yield the desired terpolymer composition, then dissolving the terpolymer in the solvents indicated. Alternatively, the Standard Solution as described above is made by Union Carbide Corporation and can be obtained from them under the name "VERR-40".

The other main ingredients of the coating are the catalyst, the antithrombotic agent, and the plasticizer. These are all dissolved in the Standard Solution. Catalysts found to be useful are tetramethyl pyrazine, benzimidazole, and indazole.

A number of antithrombotic agents are known in the art depending upon the end application. These include, for example, heparin, dermatan sulfate, heparin sulfate, activated protein C, hirudin, aspirin, thrombomodulin, DHG, plasminogen activators such as streptokinase and urokinase, aprotinin, nafamostat mesilate, gabexate mesilate and various other protease inhibitors. The preferred antithrombotic agents used in the practice of the present invention include benzothiazolol, salicylaldoxime, ricinoleic acid, glyoxalbis (2-hydroxyanil), N-(2-hydroxyethyl) pyrrolidine, and pinacol.

Another ingredient often required is a plasticizer, to keep the coating flexible enough for use on plastic sheet or film. A suitable plasticizer consists of epoxidized soybean oil, sold by Union Carbide as "FLEXOL plasticizer EPO".

In the examples to be described, all ingredients have been chosen to make up a homogeneous solution. Also, a solvent is generally required to dissolve all the ingredients and form a homogenous solution. Example solvents, depending upon the particular starting ingredients, include toluene and methyl ethyl ketone.

A variety of techniques are available for applying the coating to the medical instrument or device including dipping, spraying, and painting. In the examples described below the small experimental samples were simply dipped for one second in the coating solution, removed, and dried.

Figure 2:
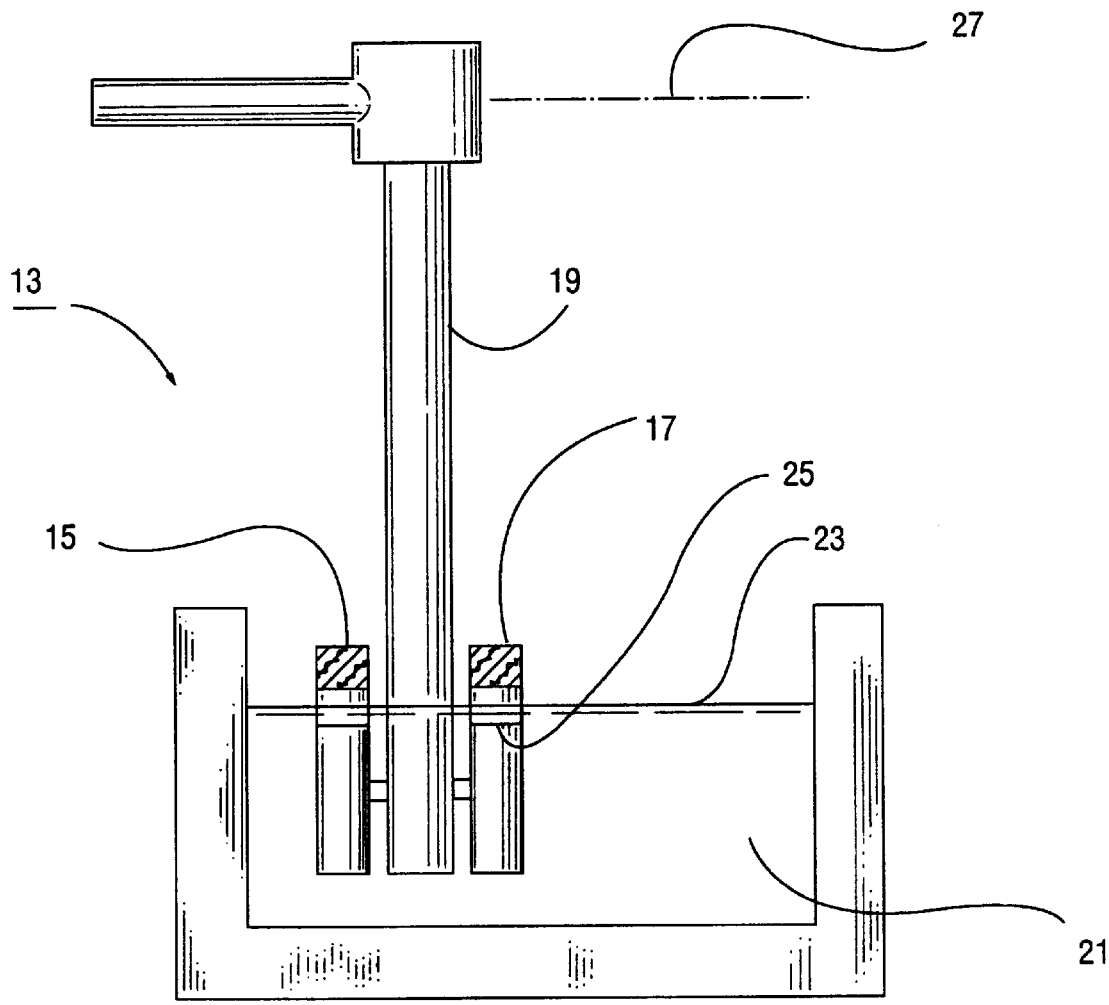
FIG. 2 is a simplified diagram of the test apparatus used in evaluating the coagulation times for blood in contact with materials treated according to the method of the invention.

After the coating has been applied to the plastic and dried, it must be determined whether the coating is resistant to the coagulation of blood in contact with it. The well-known technique of tipping a test tube containing blood is used at this point, but with several improvements which make the method more reliable. FIG. 2 of the drawings shows the apparatus 13 used for comparing the coagulation times for blood in contact with a treated plastic strip and that for blood in contact with an untreated control strip. The corked test tubes 15, 17 in FIG. 2 are 75 mm long by 12 mm in outer diameter standard size Pyrex tubes. These are fastened to the center wooden rod 19 with rubber bands or masking tape (not shown). The constant temperature water bath 21 is set at 37° C. A 10 mm by 70 mm coated plastic strip is placed in one tube and an uncoated control strip of the same size is placed in the other tube. The 10 mm wide plastic strips fit perfectly along the inner diameter of the tubes. The water level in the bath is indicated at 23 in FIG. 2 while the blood level in the test tubes is indicated at 25.

The center rod and the attached test tubes are rotated upward to a horizontal position every 10 or 20 seconds in order to check for clotting. Each tube contains a 3 ml sample of blood drawn from the same dog. Using a stopwatch the time of initial clotting for each sample is determined.

One advantage of the test apparatus illustrated in FIG. 2 is that both tubes containing the blood samples will be immersed in the bath for exactly the same length of time, because both tubes are fastened to the same rod and therefore must descend into and lift out of the bath at the same time. Also, since both tubes are fastened to the same rod, they will be lifted to exactly the same angle when inspecting for clotting.

The details of the practice of this invention are illustrated in the following examples. Although the examples illustrate the application of the novel coatings to plastic film or sheeting, the same coatings can be applied to almost any shape of medical plastic article using well known techniques, including the polyurethane sheet shown in FIG. 1.

EXAMPLE I

A commercial type of plasticized vinyl film commonly called "bag film" was used in this example. Film thickness was 0.017 inch. The coating applied contained 50 ml of the Starting Solution described above plus the following other ingredients: 18 ml methyl ethyl ketone, 12 ml toluene, 9 ml epoxidized soybean oil plasticizer (Union Carbide's FLEXOL EPO), 3 g tetramethyl pyrazine, and 3 g pinacol. The last two ingredients are the catalyst and the antithrombotic agent, respectively. These ingredients made up a clear, homogeneous solution. It is of interest that tetramethyl pyrazine has been used as a flavoring ingredient and sweetener for food (Fr. Demande 2,128,744 (1972)).

A 10 by 100 mm sample of this film was dipped for one second in the coating solution, allowed to dry in air for one half hour at room temperature, and then enclosed for two hours in a Pyrex test tube which was immersed in a constant temperature water bath at 60° C. The coated, dried sample was smooth, transparent, and non-tacky. The weight gain due to the coating was 30.2 percent of the original sample weight.

A 10 mm by 70 mm test sample of the dried, coated film was placed in one test tube of the apparatus shown in FIG. I, and a control sample of uncoated film of the same size was placed in the other test tube. Both tubes were stoppered (cork stoppers) and immersed to the level shown in FIG. 2 in a water bath at 37° C. Both tubes were raised simultaneously from the bath every ten or twenty seconds (by rotating the apparatus around the axis designated as 27 in FIG. 2) in order to visually inspect for clotting. The time of initial clotting, measured with a stopwatch, was 1.58 minutes for the tube with the control sample, and 3.33 minutes for the tube containing the coated sample. Hence the coated sample required 153 percent longer for initial clotting than the control sample.

EXAMPLE 2

A 10×100 mm sample of the same type of commercial bag film described in Example 1 was employed. The coating applied contained 50 ml of the Starting Solution plus the following additions: 12 ml toluene, 18 ml methyl ethyl ketone, 0.3 g glyoxalbis(2-hydroxyanil) (antithrombotic agent), 3 g tetramethyl pyrazine (catalyst), and 9 ml epoxidized soybean oil plasticizer.

The sample was dipped for one second in the coating solution, then dried one half hour in air at room temperature, followed by two hours at 60° C. as discussed above. The dried, coated sample was smooth, transparent, and non-tacky. The weight gain was 29.2 percent due to the presence of the coating.

A coated sample cut to proper size was placed in one tube of the apparatus in FIG. 2, while a similar uncoated sample was placed in the other tube. Both tubes were raised from and lowered into the bath simultaneously as described above. The untreated control sample displayed initial coagulation at 95 seconds, while the corresponding time for the coated sample was 130 seconds. This represents an increase of 37 percent in the time of initial coagulation.

EXAMPLE 3

Another 10×100 mm sample of the bag film described in Example I was used. The coating solution consisted of the Starting Solution plus 12 ml toluene, 18 ml methyl ethyl ketone, 9.0 ml epoxidized soybean oil, 3 g benzothiazolol (antithrombotic agent), and 2 g indazole (catalyst). The sample was dipped in the coating solution for one second at room temperature, and then dried at room temperature and at 60° C. as described above. The gain in weight due to the coating was 23.5 percent. The coated sample was smooth, transparent, and slightly tacky.

The coated sample was placed in one tube of FIG. 2 and an uncoated control sample was placed in the other tube. Both tubes were raised from and lowered into the 37° C. bath every 10 or 20 seconds using the apparatus in FIG. 2. Initial clotting occurred at 2.50 minutes for the untreated sample and at 4.50 minutes for the coated sample, representing an 80 percent increase in initial coagulation time. The source of the blood was a 22 kg male dog.

EXAMPLE 4

Another 10×100 mm sample of the bag film described in Example I was employed in this example. The coating solution included the Starting Solution plus 12 ml toluene, 18 ml methyl ethyl ketone, 9.0 ml epoxidized soybean oil, 3 g benzothiazolol (antithrombotic agent), and 0.5 g benzimidazole (catalyst). The sample was dipped in the coating solution for one second, the dried at room temperature and at 60° C. as usual.

The gain in weight due to the coating was 31.0%. The coated sample was smooth, colorless, and non-tacky. A coated test sample of the proper size was placed in one tube of the test apparatus, and the uncoated control sample of the same film was placed in the other tube. The tubes were alternately raised from and lowered into the bath as described above. Initial clotting took place at 3.00 minutes for the control sample and at 4.50 minutes for the test sample, corresponding to an increase of 50 percent in coagulation time. The blood used was drawn from a 20 kg male dog.

EXAMPLE 5

A 10×100 mm sample of polycarbonate-based polyurethane film reported to have superior hydrolytic and oxidative stability was used in this example. Film thickness was 0.019 inch. The coating used contained the Starting Solution plus 12 ml toluene, 18 ml methyl ethyl ketone, 3 g tetramethyl pyrazine (catalyst), 3 g pinacol (antithrombotic agent), and 9 ml epoxidized soybean oil. The sample was dipped in the coating solution for one second, then dried at room temperature and at 60° C. as described in previous examples.

Its coagulation was compared with a sample of the uncoated urethane film, using the same apparatus as before. The blood in the test tube containing the coated sample showed initial coagulation at 2.58 minutes, compared to 1.13 minutes for the blood containing the control sample. This corresponds to a 128 percent increase in initial coagulation time for the treated sample. The source of the blood was a 32 kg male dog.

EXAMPLE 6

A 10×100 mm sample of the 0.019 inch polycarbonate-based polyurethane sheet described in the previous example was employed. The coating contained the Starting Solution plus 12 ml toluene, 18 ml methyl ethyl ketone, 3 g benzothiazolol (antithrombotic agent), 2 g indazole (catalyst), and 9 ml epoxidized soybean oil. The sample was dipped in the coating solution for one second, then dried at room temperature and at 60° C. as usual.

Its initial coagulation time was compared with that of an untreated sample of the same material using the usual apparatus. The initial clotting time for the coated sample was 3.08 minutes, compared with 1.75 minutes for the uncoated control sample. This amounts to a 76 percent increase in initial clotting time for the coated sample. The blood used in the test came from a 40 kg male dog.

One additional technique was employed in this example. Before the polycarbonate-based polyurethane sample was coated as described above, it was first immersed in a one percent solution of hexamethylene diisocyanate in ethanol for one hour and allowed to dry overnight. The polyisocyanate provided what is sometimes called a "tie-coat", and resulted in a tighter bonding of the outer thromboresistant coating. The tie-coat can provide a valuable variation on the usual procedure previously described. Such a polyisocyanate tie-coat has been used by Beavers for bonding an optical coating to contact lenses (U.S. Pat. No. 4,663,233); by Kliment for bonding polymeric coatings to medical instruments (U.S. Pat. No. 4,729,914); and by Takagi for bonding a special coating to medical tubing (U.S. Pat. No. 4,378,803).

EXAMPLE 7

A 10×100 mm sample of the polycarbonate-based polyurethane film described in the previous example was used. The coating solution contained the Starting Solution plus 12 ml toluene, 18 ml methyl ethyl ketone, 3 g N-(2-hydroxyethyl) pyrrolidine (antithrombotic agent), 0.5 g tetramethyl pyrazine (catalyst), and 9 ml soybean oil plasticizer. The sample was dipped in the coating solution for one second, then dried at room temperature and at 60° C. as before.

Its initial coagulation time was compared with that of an untreated sample of the same film employing the usual apparatus. The initial coagulation time for the coated sample was 2.08 minutes, compared with 0.83 minutes for the un-coated sample. This represents an increase of 151 percent in initial coagulation time for the coated sample. The blood employed in the test was obtained from a 31 kg female dog.

EXAMPLE 8

A 10×100 mm sample of an 0.011 inch modified polyurethane film having excellent tensile strength, chemical stability, and radiation resistance was used in this example. The coating formulation contained the "Starting Solution" plus 12 ml toluene, 18 ml methyl ethyl ketone, 3 g tetramethyl pyrazine (catalyst), 3 g pinacol (antithrombotic agent), and 9 ml epoxidized soybean oil. The sample was dipped for one second in the coating solution, then dried at room temperature and at 60° C. as discussed.

Its coagulation behavior was compared with that of a similar sample of uncoated film of the same thickness. Initial coagulation times for the coated and uncoated samples were obtained with the usual apparatus. The time for the coated sample was 2.58 minutes versus 1.13 minutes for the uncoated sample. This represents an increase of 66 percent in initial coagulation time caused by the coating. The blood for this test was drawn from a 24 kg dog.

EXAMPLE 9

A 10×100 mm sample of the 0.011 inch modified polyurethane film described in the preceding example was used. The coating formulation consisted of the "Starting Solution" plus 12 ml toluene, 18 ml methyl ethyl ketone, 3 g tetramethyl pyrazine (catalyst), 3 g ricinoleic acid (antithrombotic agent), and 9 ml epoxidized soybean oil. The sample was dipped for one second in the coating solution, removed and dried at room temperature and at 60 degrees C as described above.

Its coagulation behavior was compared with that of a similar sample of uncoated film (control sample) of the same thickness. Times of initial coagulation for the coated and uncoated samples were obtained with the apparatus described above. Initial coagulation time for the coated sample was 3.33 minutes compared to 2.17 minutes for the uncoated sample. These figures indicate an increase of 53 percent in initial coagulation time caused by the coating. The blood for this test was drawn from a 25 kg male dog.

An invention has been provided with several advantages. In contrast to the prior art practice of periodic administration of antithrombotic agent orally or intravenously, the technique described in the present invention provides a surface coating prepared by reacting a specially selected thromboresistant agent and a base polymer. The thromboresistant agent being thus captured in a polymeric matrix provides a product which has a long-term usefulness limited only by the stability of the bound antithrombotic agent. The technique of the invention restricts the antithrombotic agent to the (foreign) surface of the plastic, so that the inhibitory effect of the agent is exercised at the exact location where the platelets become activated by surface contact and also at the exact location where the coagulation is initiated.

The prior art venous injection technique allows the blood to carry the injected antithrombotic agent to all parts of the body. In the practice of the present invention the agent is present in the coating for the device and being thus bound is prevented from spreading to other parts of the body.

The technique is reliable, cost effective and can be easily performed with commonly available starting materials.

While the invention has been shown in only one of its forms, it is not thus limited but is susceptible to various changes and modifications without departing from the spirit thereof.

What is claimed is:

1. A thromboresistant plastic article for use in contact with blood or blood products, the thromboresistant plastic article comprising:
   an organic polymeric body formed with at least one exposed surface for contacting blood or blood products, the exposed surface of the body having a surface coating applied thereto, the surface coating comprising the reaction product of a base polymer containing epoxy groups and an antithrombotic agent containing hydroxyl groups;
   wherein the antithrombotic agent is selected from the group consisting of benzothiazolol, salicylaldoxime, ricinoleic acid, glyoxalbis(2-hydroxyanil), N-(2-hydroxyethyl) pyrrolidine, pinacol, and combinations thereof; and
   wherein the surface coating further comprises a catalyst which promotes a reaction between the epoxy groups of the base polymer and the hydroxyl groups of the antithrombotic agent and a solvent for forming a homogeneous solution of the base polymer, antithrombotic agent and catalyst.

2. The thromboresistant plastic article of claim 1, wherein the catalyst is selected from the group consisting of tetramethyl pyrazine, benzimidazole, and indazole.

3. The thromboresistant plastic article of claim 1, wherein the base polymer is prepared by polymerizing glycidyl methacrylate as a reactive monomer having an epoxy group as a reactive functional group.

4. The thromboresistant plastic article of claim 1, wherein the base polymer is a terpolymer having the following approximate percentage composition of monomers by weight, based on the total weight of terpolymer: 82% vinyl chloride, 9% vinyl acetate and 9% glycidyl methacrylate.

5. The thromboresistant plastic article of claim 1, further comprising a plasticizer.

6. The thromboresistant plastic article of claim 1, wherein the body which is rendered thromboresistant is selected from the group consisting of catheters, sutures, blood bags, intra-aortic balloons, soft tissue prothesis, hard tissue prothesis, artificial heart and artificial organs.

7. A method of forming a thromboresistant polymeric article for use in contact with blood or blood products, the thromboresistant polymeric article being comprised of a polymeric body formed with at least one exposed surface for contacting blood or blood products, the method comprising the steps of:

preparing a solution which includes as ingredients at least a base polymer having reactive epoxy functional groups and an antithrombotic agent having reactive hydroxyl functional groups;

allowing the base polymer and the antithrombotic agent to react in solution to thereby form as a reaction product a surface coating which will adhere to the exposed surface of the polymeric body;

applying the surface coating to at least a portion of the exposed surface of the polymeric body; and wherein the antithrombotic agent is selected from the group consisting of benzothiazolol, salicylaldoxime, ricinoleic acid, glyoxalbis(2-hydroxyanil), N-(2-hydroxyethyl) pyrrolidine, pinacol, and combinations thereof.

8. The method of claim 7, wherein the surface coating is applied to the exposed surface of the polymeric body by dipping, spraying or painting.

9. The method of claim 7, wherein the surface coating is applied to the exposed surface of the polymeric body by dipping the polymeric body in a container of the surface coating, the coating then being allowed to dry at room temperature.

10. The method of claim 7, wherein the solution of the base polymer having reactive epoxy functional groups and the antithrombotic agent having reactive hydroxyl functional groups is allowed to stand for a period of time sufficient to allowed the reaction product to be formed prior to applying the surface coating to the exposed surface of the polymeric body.

11. A method of forming a thromboresistant polymeric article for use in contact with blood or blood products, the thromboresistant polymeric article being comprised of a polymeric body formed with at least one exposed surface for contacting blood or blood products, the method comprising the steps of:

preparing a solution which includes as ingredients at least a base polymer having reactive epoxy functional groups, an antithrombotic agent having reactive hydroxyl functional groups, a catalyst which promotes a reaction between the epoxy groups of the base polymer and the hydroxyl groups of the antithrombotic agent and a solvent for forming a homogeneous solution of the base polymer, antithrombotic agent and catalyst;

allowing the base polymer and the antithrombotic agent to react in solution to thereby form as a reaction product a surface coating which will adhere to the exposed surface of the polymeric body;

applying the surface coating to at least a portion of the exposed surface of the polymeric body; and wherein the antithrombotic agent is selected from the group consisting of benzothiazolol, salicylaldoxime, ricinoleic acid, glyoxalbis(2-hydroxyanil), N-(2-hydroxyethyl) pyrrolidine, pinacol, and combinations thereof.

12. The method of claim 11, wherein the catalyst is selected from the group consisting of tetramethyl pyrazine, benzimidazole, and indazole.

13. The method of claim 11, wherein the base polymer is prepared by polymerizing glycidyl methacrylate as a reactive monomer having an epoxy group as a reactive functional group.

14. The method of claim 11, wherein the base polymer is a terpolymer having the following approximate percentage composition of monomers by weight, based on the total weight of terpolymer: 82% vinyl chloride, 9% vinyl acetate and 9% glycidyl methacrylate.

15. The method of claim 11, further comprising a plasticizer.

16. The method of claim 11, wherein the body which is rendered thromboresistant is selected from the group consisting of catheters, sutures, blood bags, intra-aortic balloons, soft tissue prothesis, hard tissue prothesis, artificial heart and artificial organs.

17. A thromboresistant article for use in contact with blood or blood products, the thromboresistant article comprising:

a body formed with at least one exposed surface for contacting blood or blood products, the exposed surface of the body having a surface coating applied thereto, the surface coating comprising the reaction product of a base polymer containing epoxy groups and an antithrombotic agent containing hydroxyl groups;

wherein the antithrombotic agent is selected from the group consisting of benzothiazolol, salicylaldoxime, ricinoleic acid, glyoxalbis(2-hydroxyanil), N-(2-hydroxyethyl) pyrrolidine, pinacol, and combinations thereof; and wherein the surface coating further comprises a catalyst which promotes a reaction between the epoxy groups of the base polymer and the hydroxyl groups of the antithrombotic agent and a solvent for forming a homogeneous solution of the base polymer, antithrombotic agent and catalyst.

\* \* \* \* \*